(12) United States Patent
Zhou et al.

(10) Patent No.: US 11,920,179 B2
(45) Date of Patent: *Mar. 5, 2024

(54) VIRUS-ASSISTED ALGAL CELL DISRUPTION FOR COST-EFFECTIVE BIOFUEL PRODUCTION

(71) Applicant: Purdue Research Foundation, West Lafayette, IN (US)

(72) Inventors: Zhi Zhou, West Lafayette, IN (US); Zhe Sun, West Lafayette, IN (US)

( * ) Notice: Subject to any disclaimer, the term of this patent is extended or adjusted under 35 U.S.C. 154(b) by 216 days.

This patent is subject to a terminal disclaimer.

(21) Appl. No.: 17/491,636

(22) Filed: Oct. 1, 2021

(65) Prior Publication Data

US 2022/0056493 A1 Feb. 24, 2022

Related U.S. Application Data

(63) Continuation of application No. 16/875,299, filed on May 15, 2020, now Pat. No. 11,149,290.

(60) Provisional application No. 62/849,050, filed on May 16, 2019.

(51) Int. Cl.
*C12N 1/12* (2006.01)
*C12P 7/6463* (2022.01)

(52) U.S. Cl.
CPC .............. *C12P 7/6463* (2013.01); *C12N 1/12* (2013.01)

(58) Field of Classification Search
CPC .................................. C12N 1/12; C12P 7/6463
See application file for complete search history.

(56) References Cited

U.S. PATENT DOCUMENTS 9,109,239 B2 * 8/2015 Franklin .............. C12N 9/0071
11,149,290 B2 * 10/2021 Zhou ..................... C12N 1/12

OTHER PUBLICATIONS

U.S. Appl. No. 16/875,299, filed May 15, 2020.
Chen, Z., Zhang, B., Zhang, J., Lei, X., Zhang, H., Li, Y., Yang, L., Zheng, W., Tian, Y, and Boughner, L.A. (2015) A lytic bacterium's potential application in biofuel production through directly lysing the diatom Phaeodactylum tricornutum cell. Algal research 12, 197-205.
Chen, Z., Zhang, J., Lei, X., Zhang, B., Cal, G., Zhang, H., Li, Y., Zheng, W., Tian, Y. and Xu, H. (2014) Influence of plaque-forming bacterium, *Rhodobacteraceae* sp. on the growth of Chlorella vulgaris. Bioresource technology 169, 784-788.
Cheng, Y.-S., Labavitch, J. and VanderGheynst, U.S. (2015) Organic and Inorganic nitrogen impact Chlorella variabilis productivity and host quality for viral production and cell lysis. Applied biochemistry and biotechnology 176(2), 467-479.
Cheng, Y.-S., Zheng, Y., Labavitch, J.M. and VanderGheynst, U.S. (2013) Virus infection of Chlorella variabilis and enzymatic saccharification of algal biomass for bioethanol production. Bioresource technology 137, 326-331.
Sanmukh, S.G., Khairnar, K., Chandekar, R.H. and Paunikar, W.N. (2014) Increasing the extraction efficiency of algal lipid for biodiesel production: Novel application of algal viruses. African Journal of Biotechnology 13(15).

* cited by examiner

*Primary Examiner* — Tekchand Saidha
(74) *Attorney, Agent, or Firm* — Woodard, Emhardt, Henry, Reeves & Wagner, LLP

(57) ABSTRACT

An efficient virus based wet biomass lipid extraction system is disclosed herein. The system includes a microalgal biomass which is inoculated with a matched algal virus. The biomass is then incubated under conditions resulting in the algal virus infecting the algae cells and proliferating to the point that the algae cells are disrupted. This releases lipids such that they may be collected by conventional techniques, including solvent extraction. In an exemplary embodiment, the microalgal biomass comprises *Chlorella* sp, and the virus was Chlorovirus Paramecium bursaria chlorella virus (PBCV-1).

20 Claims, 7 Drawing Sheets

VIRUS-ASSISTED ALGAL CELL DISRUPTION FOR COST-EFFECTIVE BIOFUEL PRODUCTION

FIELD

The present application relates to biofuel production from wet biomass. Particularly, viral infection of microalgae is used as a natural cell disruption method for obtaining lipids used in algal biofuel production.

BACKGROUND

Biofuel production from microalgae has been advocated as one of the potential alternative energy sources that is sustainable and environmentally friendly. Lipid extraction has been identified as one of the most cost and energy intensive steps during the production of algal biofuel. Various disruption methods have been developed to maximize the lipid extraction, but most of them are economically infeasible to scale-up due to the requirement of extreme conditions and high costs.

This section introduces aspects that may help facilitate a better understanding of the disclosure. Accordingly, these statements are to be read in this light and are not to be understood as admissions about what is or is not prior art.

Rapid industrialization and human population growth have resulted in the depletion of fossil fuels and rising of $CO_2$ emissions, which have promoted the development of sustainable and environmental friendly biofuels. Compared with other energy crops commonly used for biofuel production, microalgae have shown advantages on high growth rate, low arable land use, and high lipid content. Lipids in microalgae, serving as the reservoir of carbon and energy in microalgal cells, are enveloped in droplets within microalgae's cytoplasm and protected by rigid algal cell walls.

In order to exploit these intracellular lipids for biofuel production, many methods have been developed for microalgal lipid extraction at laboratory scale, but these methods are usually associated with high extraction costs. Depending on the type of microalgal biomass applied in the extraction process, these extraction techniques can be categorized into dry biomass and wet biomass based extraction methods. Dry extraction is currently technologically mature but the energy intensive drying/dehydration process has made wet extraction a competitive alternative. Wet extraction skips the energy intensive dehydration step. However, a cell disruption pretreatment is required to break rigid algal cell walls and neutralize the surface charge of algal cells to secure the lipid yield.

So far, diverse cell disruption methods based on physical, chemical, and biological processes have been developed, but large-scale application of these methods is still restricted by high cost. Physical disruption methods such as bead-beating, high pressure homogenization (HPH), ultrasonication, microwave and electroporation have been developed to break cell walls physically. Chemical disruption methods depend on chemical reactions to lyse or break algal cell walls. Physical disruption methods demand intensive energy to support their thermal, electrical or mechanical treatments, while chemical disruption methods are less energy intensive and easier to scale-up. However, great demands of chemicals, need of chemical waste treatment and disposal, as well as potential equipment corrosion remain, challenging the economic performance of chemical disruption.

Biological disruption methods are based on the idea of enzymatic degradation of cell walls, which can be processed under mild reaction conditions with high selectivity. Actually, various types of microalgae even with very resistant layers are able to be lysed by a specific mixture of enzymes at relevant energy cost. The limitation of enzymatic cell disruption, however, is the high cost of enzyme processing. The combination of different disruption methods such as thermal disruption and enzymatic disruption could achieve higher lipid extraction efficiency, but the inherent constraints of the energy demand for thermal disruption and the high enzyme cost still exist.

For these reasons, innovative disruption techniques characterized by low cost and high disruption efficiency should be developed.

SUMMARY

This disclosure provides a method of extracting lipid from a wet microalgal biomass. In one aspect, the method comprises inoculating the wet microalgal incubating the matched virus with the wet microalgal biomass to initiate virus infection and replication, continuing to incubate the matched virus with the wet microalgal biomass until the virus replication has disrupted at least 90% of the microalgae cells within the wet microalgal biomass, and collecting crude lipids released from the disrupted microalgae cells. In embodiments, the method used a biomass that is as much as 99% water, and the matched virus is added to the microalgal biomass at a virus-to-algae ration of at least $1.46 \times 10^{-8}$. The cell disruption may proceed to disrupt 99.99% or more of the algae cells in the biomass. In some preferred embodiments the method uses microalgal *Chlorella* sp in 99% water as the wet biomass and uses Paramecium bursaria chlorella virus (PBCV-1).

It is an object of the present invention to provide a method for deriving lipids from algae, which has lower costs than the use of enzymes required in biological methods.

Another object of the present invention is to obtain lipids from algae without requiring the continuous input of energy and chemicals common to mechanical and chemical disruption methods.

It is an advantage of the present invention that the algal viruses which are used can be acquired and maintained with minimal costs.

Further forms, objects, features, aspects, benefits, advantages, and embodiments of the present invention will become apparent from a detailed description and drawings provided herewith.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures. The attached drawings are for purposes of illustration and are not necessarily to scale.

DETAILED DESCRIPTION

Figure 1:
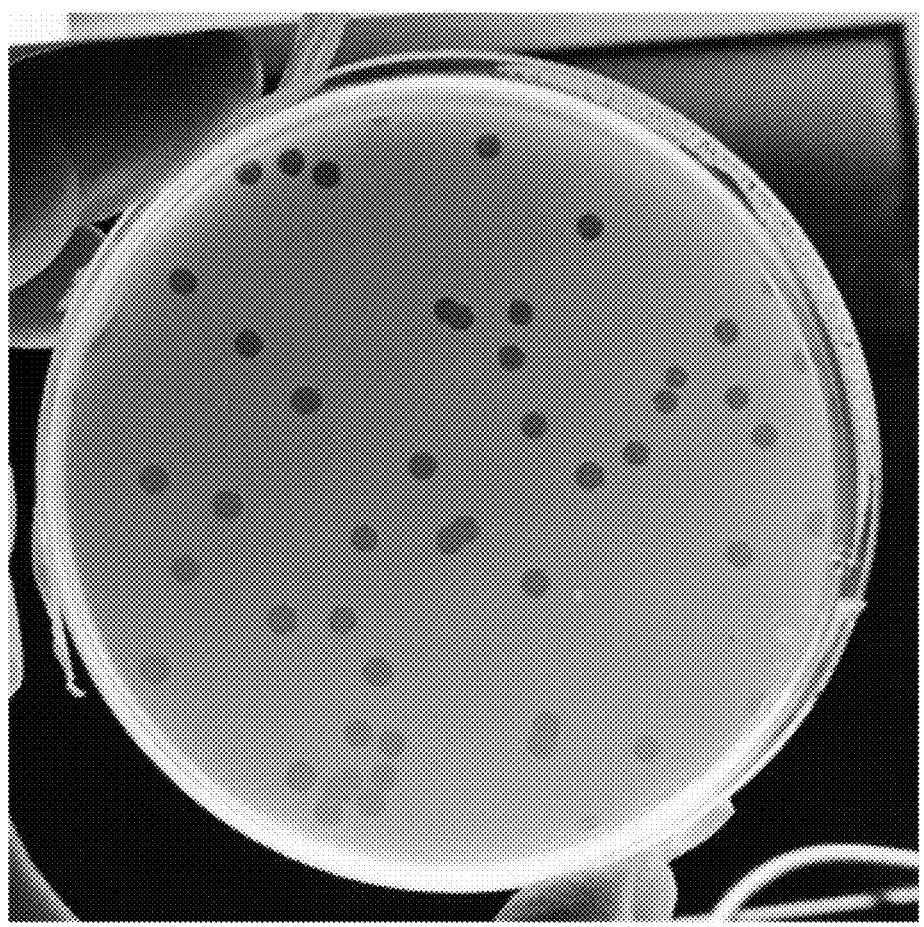
FIG. 1 is a picture of a plaque assay showing clear plaque forming units of Chlorovirus on a green layer of *Chlorella* sp.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Host-Virus System

The present invention involves the use of a host-virus system in which the host cells are infected, and eventually ruptured, by a virus provided for that purpose. A typical viral infection starts with the attachment of virus on the host cell followed by the injection of viral DNA. Then the transcription system within the host algal cell is reprogrammed by viral DNA to produce and assemble new virus particles. In particular, the present invention is directed to a host-virus system comprising a microalgal biomass and a matched algal virus.

Unlike other conventional disruption methods which are chemical and energy intensive, this approach can be triggered by trace amounts of virus and accomplish essentially complete disruption in several days using normal growth conditions. With less energy input, this viral disruption approach exhibits comparable performance to traditional disruption methods, which improves the extraction efficiency significantly from undisrupted wet biomass. Moreover, viral disruption significantly reduces the mechanical strength and increases the solvent permeability of algal cells.

In general, using viral infection to disrupt algal cells does not require the continuous input of energy and chemicals in mechanical and chemical disruption methods. The cost of algal viruses is also lower than the enzymes required in biological methods. Disclosed herein are systems and methods for the economical disruption of cells for use in a method for biofuel production. Viral infection of microalgae is used as an economical cell disruption method of wet lipid extraction in algal biofuel production.

In an exemplary embodiment, Chlorovirus Paramecium bursaria chlorella virus (PBCV-1) was isolated from a natural water system and was used to infect *Chlorella* sp. This system was used as it was a common and well understood microalgae-algal virus system. The algal suspension had approximately 99% water content. An ultrasonic disruption method was used as a reference. Viral disruption with multiplicity of infection ("MOI") $10^{-8}$ was able to disrupt all algal cells in 6 days.

Lipid yield as well as lipid composition were determined after all microalgal cells were lysed. This new cell disruption method for microalgae was determined to allow crude lipid extraction in an efficient and economic method for extracting lipids from wet algal biomass. This also demonstrated that viral disruption can significantly reduce the mechanical strength and increase the solvent permeability of algal cells.

Lipid yield with viral disruption increased more than 3 times compared to no disruption, and was also slightly higher than the lipid yield obtained from ultrasonic disruption alone at optimal conditions. Moreover, the quality of extracted lipids was not affected by viral infection. Most importantly, compared to the extensive energy and chemical input required by previous disruption methods, the cost of viral disruption is negligible. Taken together, the results confirmed the feasibility of applying viral infection to disrupt algal cells for lipid extraction as a method for cost-efficient biofuel production. In particular embodiments, the system operates in the absence of other disruption mechanisms, or it may be supplemented with sonication or other approaches.

Microalgal Biomass

The biomass used in the present invention is a wet, microalgal biomass. The microalgae contained in the biomass may be any comprising algae cells that can be infected, and ultimately disrupted, by a matched virus. The wet biomass may include a wide range of percentages of water. The concentration may, for example, be at least 90% water by weight, preferably at least 95% water, and more preferably at least 99% water.

Generally, any concentration is useful, but the concentration may affect yield. Persons of ordinary skill in the art will be able to select concentrations suitable to make the process acceptable in terms of desired costs, yield, use of materials, duration and the like.

Algal Virus

The host-virus system uses a virus that is "matched" to the host algae. A matched virus is one that infects the algal cells and proliferates to the point of disrupting (lysing) the algae cells. A matched virus is one that meets the limitations discussed herein as to causing the cell disruption in a desire time frame.

As used herein, the term "matched virus" is not limited to a single species or strain of virus for a given system. For example, different plaques may be formed by different types of Chlorovirus as various species of Chlorovirus have been detected and isolated. Thus, the matched algal virus may include a combination of two or more species or strains which together constitute the algal virus used with a given microalgal biomass. However, in order to minimize unpredictable infection behavior caused by a mixed Chlorovirus community, the Chlorovirus stock exemplified herein was established from a single plaque and identified to be PBCV-1 with PCR.

Amount of Virus

Figure 4:
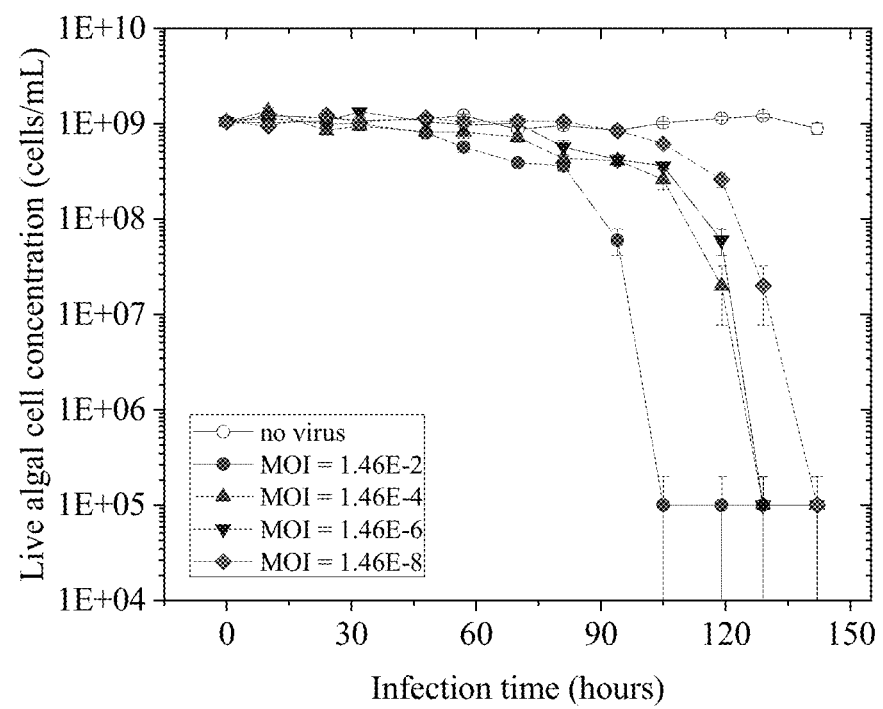
FIG. 4 is a graph showing infection behavior of concentrated microalgal biomasses with different multiplicity of infection (MOI).

The amount of virus added to the biomass, the "virus-to-algae" ratio, may be any amount sufficient to provide the desired extent of cell disruption within the desired amount of time. For example, in certain embodiments the matched algal virus is inoculated into the microalgal biomass at a virus-to-algae ration of at least $1.46 \times 10^{-8}$. As shown in FIG. 4, virus-to-algae ratios (a.k.a. multiplicity of infection (MOI)) ranging from $1.46 \times 10^{-8}$ to $1.46 \times 10^{-2}$ were demonstrated to be effective. Even at a very low initial MOI of $1.46 \times 10^{-8}$, viruses still successfully infected algal cells with only a delay of 30 hours, because the viruses reproduced and synthesized new viruses quickly. The result of viral infection at such a low initial concentration indicated that using viruses for algal biomass treatment can be a robust technique for industrial application. Continuous operation and effluent recycling can help maintain a high virus concentration in industrial processes.

The host-virus system we used in this work is fresh water microalgae *Chlorella* sp. and related virus PBCV-1. The algal biomass is treated using a virus effective to infect the microalgal biomass. Other algal viruses are also useful in accordance with the present method, particularly those that can infect algal species with high lipid content.

Incubation Parameters

The microalgal biomass and matched algal virus may be obtained in conventional fashions. The host-virus system also may be incubated using conventional incubation equipment and operating conditions. In general, the host-virus system is operated under conditions which result in the infection and proliferation of the algal virus to lyse the algae cells. Advantageously, these conditions may include typical incubation parameters, including temperature, pressure and other aspects known in the art.

The time of incubation is determined based on typical factors such as the virus-to-algae ratio of the initial inoculation, the rate of replication of the algal virus, the targeted end point in terms of percent cell disruption, etc. In accordance with the teachings herein, these parameters may be adjusted to achieve the cell disruption in the desired time. For example, the period of incubation can be less than two weeks, preferably less than one week, and more preferably less than 2-3 days.

Cell Disruption

When the number of virus particles reaches particular level, the algal cell is lysed and virus particles are released into the aqueous environment. A successful infection is able to cause the lysis of algal cell in a few hours while releasing hundreds of newly assembled virus particles that are ready for subsequent infection. Therefore, trace amounts of algal virus are able to trigger massive disruption of algal cells in ambient environment without additional input of energy and chemicals.

The incubation of the algal virus with the biomass is continued until a predetermined extent of cell disruption has occurred. In certain embodiments, for example, the process proceeds until at least 90% of the algae cells have been disrupted, preferably at least 95% of the cells, and more preferably at least 99% of the cells. As described herein, in another embodiment the algal virus was incubated with the biomass until more than 99.99% of the algae cells were disrupted.

Solvent Extraction

The purpose of the cell disruption is to facilitate recovery of lipids from the algae cells, such as for use in biofuels. The released lipids may be collected by a variety of known techniques. The collection may include using centrifugation to separate the disrupted biomass into a solid phase and a supernatant. In one approach, exemplified herein, the lipids are then recovered by solvent extraction from the supernatant. By way of example, the lipids in the Example were captured using chloroform as the solvent. In some embodiments, the obtained crude lipids are transesterified to the form of fatty acid methyl esters (FAMEs).

The viral disruption system was shown to provide good yields of lipids. The yield of lipids by viral disruption were compared with the yield from sonication for the same batch of algal cells. Sonication is the industry standard for disrupting algal biomass. The results showed that viral infection was as good as sonication (no statistical differences at a significance level of 0.5). In some preferred embodiment the aforementioned method lipids yields are about $5.2 \pm 0.2\%$ wt/wt to about $4.9 \pm 0.4\%$ wt/wt. The viral disruption technique can therefore be used to achieve good yield of lipids, while improving cost-effectiveness as compared to existing algal processing facilities the utilize sonication as the main extraction approach.

EXAMPLE

Materials and Methods

1. Microalgae Cultivation and Quantification

The host-virus system of *Chlorella* sp. and Chlorovirus was used to demonstrate the use of viral disruption for wet lipid extraction. Fresh water microalgal strain *Chlorella* sp. (ATCC 50258) was used as it is the host of the widely spread Chlorovirus. The host-virus systems of *Chlorella* and *Chlorella* viruses have been well studied genetically and biologically.

Stock culture was cultivated under a 14-h light, 10-h dark cycle in an environmental chamber at 25° C. in ATCC 847 growth medium. Light was provided by an IPOWER Super HPS 600 W lamp installed in the environmental chamber and all culture flasks were distributed at a distance of 1.1-2.1 m from the light source. ATCC medium 847 contains 1.0 g Proteose Peptone, 250 mg $NaNO_3$, 25 mg $CaCl_2$), 75 mg $MgSO_4$, 75 mg $K_2HPO_4$, 175 mg $KH_2PO_4$, 25 mg NaCl, and a drop of 1.0% $FeCl_3$ solution in 1.0 L distilled water. The growth of microalgae was determined by a hemocytometer (HAUSSER SCIENTIFIC) and a fluorescence microscope (Nikon Eclipse Ni with Plan Fluor ×40 objective). LIVE/DEAD® BacLight™ Bacterial Viability Kits were used to stain live/dead cells after viral infection. The excitation/emission wavelengths for these dyes are 480/500 nm for SYTO 9 stain (live) and 490/635 nm for propidium iodide (dead). Additionally, dry algal biomass was obtained gravimetrically after drying at 105° C. for 12 hours in an oven until there was no significant change in weight (Thermo Scientific).

2. Virus Isolation and Quantification

A water sample with Chlorovirus was collected from a lake in Celery Bog Nature Area, West Lafayette, Ind. The collected water sample was filtered through a syringe filter with 0.2 μm PTFE membrane (Thermo Scientific) to remove non-viral particles. Then Chloroviruses in the filtrate were isolated by the modified plaque assay method (Van Etten, Burbank et al. 1983), which was also used to quantify virus in this study. A mixture of 100 μL diluted filtrate (approximately 50 PFU per 100 μL), 300 μL *Chlorella* cells ($2 \times 10^8$ to $4 \times 10^8$ cells/mL), 100 μL erythromycin stock (1000 mg/L) and 5 mL of soft-agar medium was poured onto a 1.5% agar plate. Agar medium (1.5%) and soft-agar medium (0.75%) were prepared by adding 15 g and 7.5 g agar per liter ATCC 847 medium for plaque assay. After a week's incubation at 25° C., viral plaques formed on agar plate were counted. Chlorovirus from a single plaque on the algal lawn was isolated and amplified in host culture for future use. To maintain algal viruses, 300 µL filtrate was added to 100 mL host microalgae culture ($3\times10^7$ to $7\times10^7$ cells/mL). After three days' incubation, new virus stock was prepared by filtering the viral rich suspension through a 0.2 µm syringe filter. The viral rich filtrates were stored at 4° C. for future use.

The type of Chlorovirus from single plaque was identified by polymerase chain reaction (PCR). A freeze-thaw pretreatment procedure consisting of three cycles of heating at 95° C. for 2 mins and freezing to solid was used to release viral DNA. Three algal virus-specific primer sets (CVMs, PBCVs, and ATCVs) from previous study (Short, Rusanova et al. 2011) were examined to identify the isolated Chlorovirus. Each 50 µL PCR reaction contains 2 µL of the pretreated sample, 10 µM virus specific PCR primers, DreamTaq DNA Polymerase, and 10× DreamTaq green buffer. Negative controls used water to substitute the sample. All PCR reactions were performed in a Biorad 1000-Series Thermal Cycler with denaturation at 95° C. for 2 min, followed by 39 cycles of heating at 95° C. for 30 s, annealing at primer-specific temperatures for 45 s, and extension at 72° C. for 1 min. At the end of cycling, all PCR reactions were subjected to a final extension step at 72° C. for 30 min. After PCR, 8 µL of the reaction product were loaded into 1.5% Bio-rad Certified™ agarose gel stained with SYBR safe stain and subject to electrophoresis in a Bio-Rad electrophoresis cell. The electrophoresis results were obtained by Bio-Rad Gel Doc™ XR+ with Image Lab™ software.

3. Viral Disruption

The potential of viral infection as a disruption method was studied. We first investigated the viral infection behaviors under various initial virus loadings. Then we tested the physical strength and chemical resistance of algal cells before and after viral infection. To obtain concentrated algal suspensions for following experiments, algal cells at the early stationary phase were centrifuged at 3220×G for 5 min (Eppendorf Centrifuge 5810 R and FALCON 50 mL polypropylene conical tube) and then re-suspended in growth medium to achieve water content of approximately 99%. These concentrated suspensions were allocated into 1 mL aliquots for further disruption treatments.

a. Dynamics of Viral Infection

The concentrated algal suspensions were inoculated with descending virus loadings and the initial virus concentrations in inoculated suspensions were 0 (no virus inoculated), $1.66\pm0.04\times10^1$, $1.66\pm0.04\times10^3$, $1.66\pm0.04\times10^5$, and $1.66\pm0.04\times10^7$ PFU/mL, respectively. Then concentrations of live algal cells were measured twice a day for 6 days until no live algal cells could be observed in all virus infected samples. Concentrations of live cells were plotted with incubation time to obtain the infection behaviors with different initial virus loadings.

b. Electron Microscopy

To further examine the viral lead cell lysis at an ultrastructural perspective, healthy cells and infected cells (43-hour and 54 hour post infection) were observed under a Tecnai T12 transmission electron microscope (TEM). Samples were prepared by the Purdue Electron Microscopy Facility with modified method described by (Greiner, Frohns et al. 2009). Target algae suspensions were first centrifuged to obtain an algal pellet and were fixed with a cacodylate-buffered (pH6.8) 2% glutaraldehyde and 2% formaldehyde solution. After washing in buffer, samples were post-fixed in the same buffer with 2% OsO4. The samples were dehydrated in a series of graded acetone and then embedded in Embed 812 Resin. At last diamond knives were used to acquire ultrathin sections. The ultrathin sections were stained with uranyl acetate and lead citrate for TEM observation.

c. Sonication

Ultrasonic treatment was employed to evaluate the effect of viral infection on the mechanical strength of algal cells. A low frequency (20 kHz) ultrasonic processor (FB-505, Fisher Scientific) equipped with a ⅛ inch diameter ultrasonic horn was operated at 100 W input power as mechanical treatment. Cell breakage of healthy and virus disrupted algal suspensions were investigated with various sonication time treatments ranging from 0 to 420 seconds. The magnitude of cell rupture after sonication was indicated by the absorbance measurements of released intracellular material in supernatant after centrifugation at 3220×G for 5 min. The absorbance of released intracellular materials was measured by a NANODROP 2000c Spectrophotometer (Thermo Scientific) at 675 nm wavelength using ATCC 847 medium as blank. All ultrasonication treatments were done in an ice water bath to minimize the influence caused by temperature rise. All samples were prepared and measured in triplicate.

d. Lipid Extraction

The performance of lipid extraction by organic solvent was used to evaluate the effect of viral infection on the resistance of cells to chemical treatment. In this study, we modified the Bligh and Dyer method (Bligh and Dyer 1959, Teo, Jamaluddin et al. 2014) to extract lipids from wet algal biomass. The concentrated algal suspensions were first exposed to 3 experimental conditions: 1) no treatment, 2) viral infection for 5 days with m.o.i. of 0.01 and 3) 300 seconds of sonication. Then treated samples were centrifuged at 3220×G for 5 min to separate liquid phase and solid phase. Separated upper layer supernatant and bottom pellet were both subjected to lipid extraction, respectively. Acquired pellets were re-suspended in 1 mL distilled water to match the water volume of supernatant samples. These supernatant and pellet samples were mixed with 2 mL chloroform and 1 mL methanol. The chloroform layer was collected after 30 minutes of vortex, followed by centrifugation at 3220×G for 5 min. Another two rounds of extraction were implemented by adding another 2 mL of chloroform followed by same vortex and centrifugation processes to ensure complete extraction. Crude lipid was obtained by blow drying the lipid containing chloroform with nitrogen gas in a fume hood.

4. Lipid Transesterification and Quantification

Since the amount of algal biomass in our study was insufficient to provide accurate gravimetric measurements, the obtained crude lipids were transesterified to the form of acid methyl ester (FAMEs) and analyzed through GC-MS. Crude lipids obtained from each sample were subsequently transesterified with 2 mL methanol containing 5% sulphuric acid for 2 hours at 85° C. Hexane was used to extract FAMEs from the mixture (1 mL hexane per mL mixture). The hexane layer was collected after 15 minutes of vortex and 5 minutes of centrifugation at 3220×G. Two more extractions by hexane were applied to guarantee the complete extraction of FAMEs. The extracted FAMEs were analyzed by a Shimadzu GC-2010 Plus equipped with a TQ8040 mass spectrometer and a Shimadzu AOC-5000 autosampler. The GC-MS was operated at a flow rate of 1.44 mL·min$^{-1}$ using helium as the carrier gas and the source temperature of MS was set at 200° C. Each run was started with a liquid injection of 1 µL sample onto a HP-5MS (30 m×0.25 mm×0.25 μm, Angilent) column using 1:10 split ratio. The oven program was held at 80° C. for 4 minutes, ramped to 235° C. at a rate of 10° C.·min$^{-1}$, then the rate was cut down to 5° C.·min$^{-1}$ until the temperature reached 300° C. At last oven temperature was held at 300° C. for 3 minutes to drive out residues in column. Supelco 37 component FAMEs standard mix was used to identify and quantify the FAMEs in this study. Each sample was spiked with 7.52 mg·L$^{-1}$ Heptadecanoic Acid Methyl Ester (Ultra Scientific) as internal standard for GC-MS analysis. It should be noted that the peaks (Fatty acids C 16:1 and C 17:1) that not included in the standard mix were identified by the mass spectral database from the Shimadzu GC-MS and quantified according to their nearest eluting peaks in standard mix. The total lipid yield reported in this study was the sum of all detected FAMEs contents, the lipids unable to be quantified by GC-MS were not included. The MS spectrum and detected FAMEs contents were reported.

5. Statistical Analysis

The total lipid yields as well as each extracted fatty acid were compared according to the applied disruption methods using a one-way ANOVA at a significant level of $\alpha=0.05$.

Results and Discussion

1. Virus Isolation and Identification.

Figure 2:
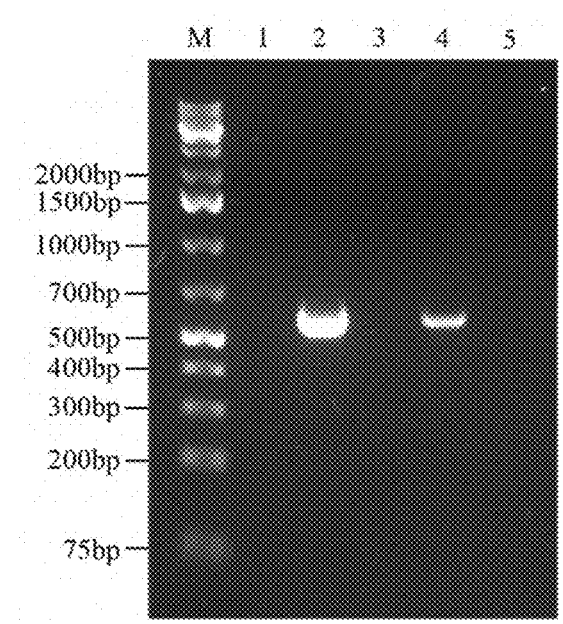
FIG. 2 is a picture of gel electrophoresis to confirm the identity of the virus.

According to FIG., the clear plaques on algal lawn were formed by Chlorovirus contained in our field sample. However, different plaques may be formed by different types of Chlorovirus as various species of Chlorovirus have been detected and isolated so far (Van Etten and Dunigan 2012). In order to minimize unpredictable infection behavior caused by a mixed Chlorovirus community, the Chlorovirus stock used in this study was established from a single plaque and identified to be PBCV-1 with PCR. FIG. 2 is a picture of gel electrophoresis to confirm the identity of the virus.

2. Viral Lysis of Algal Biomass

To the proposed viral disruption method for wet lipid extraction, wet algal biomass with approximately 99% water content was consistently used in this study. One of the reasons is that biomass with this water content could be easily obtained by some inexpensive harvest methods such as flocculation or sedimentation (Yoo, Park et al. 2012). On the other hand, albeit successful cell wall degradation of *Chlorella* sp. cells by viral infection of PBCV-1 have been observed (Meints, Lee et al. 1984, Meints, Lee et al. 1986), little information is available for the infection behavior at high algal density that is suitable for lipid extraction. Therefore, the ultrastructure and dynamics of viral infection at high algal density were investigated.

a. Ultrastructure of Viral Lysis

Figures 3A, 3B, 3C:
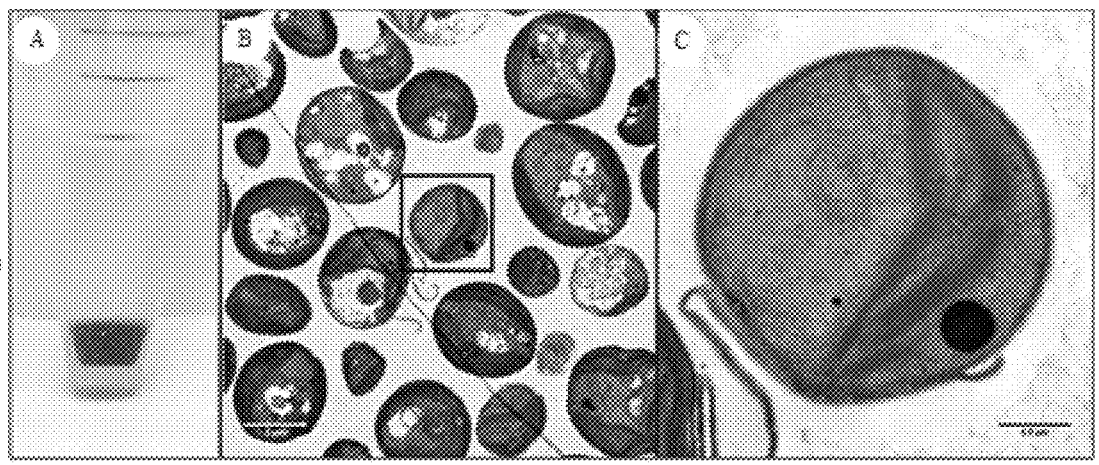
FIGS. 3A-3I include pictures of concentrated *Chlorella* cells before infection (A-C), 43 hours post infection (D-F) and 54 hours post infection (G-I). (A) Uninfected *Chlorella* cells after centrifugation; (B) TEM picture of uninfected cells; (C) Zoom view of an uninfected cell corresponding to the frame in (B); (D) Centrifuged *Chlorella* pellet 43 hours post infection; (E) TEM picture of cells 43 hours post infection; (F) Detail of one infected cell with assembled virus particles (black arrow) and empty virus capsids (white arrow) corresponding to the frame in (E); (G) Centrifuged *Chlorella* pellet 54 hours post infection; (H) TEM picture of lysed cells 54 hours post infection; (I) Enlarged cells in (H), the white arrow marks the empty attached virus capsid and degraded cell wall, and the black arrow indicates a lysed cell with a highly deteriorated cell wall.
Figures 3D, 3E, 3F:
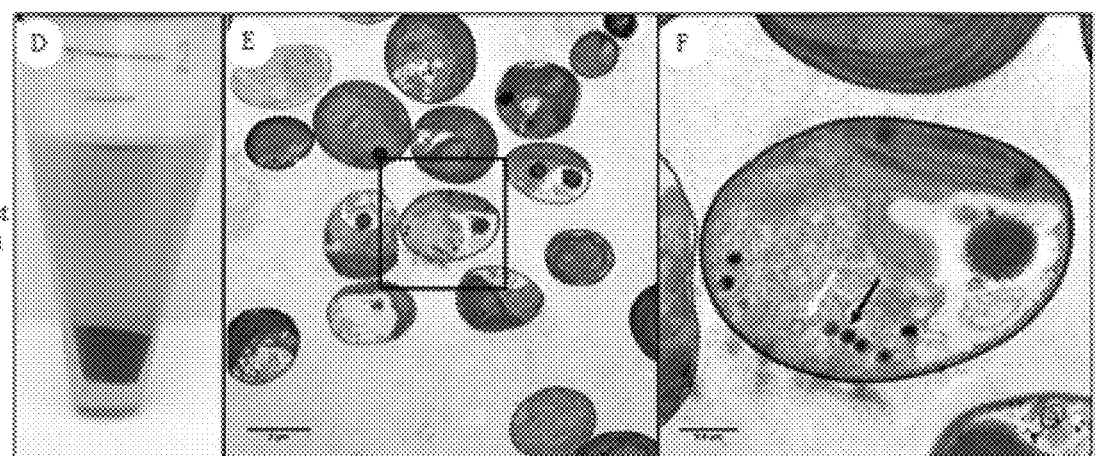
Figures 3G, 3H, 3I:
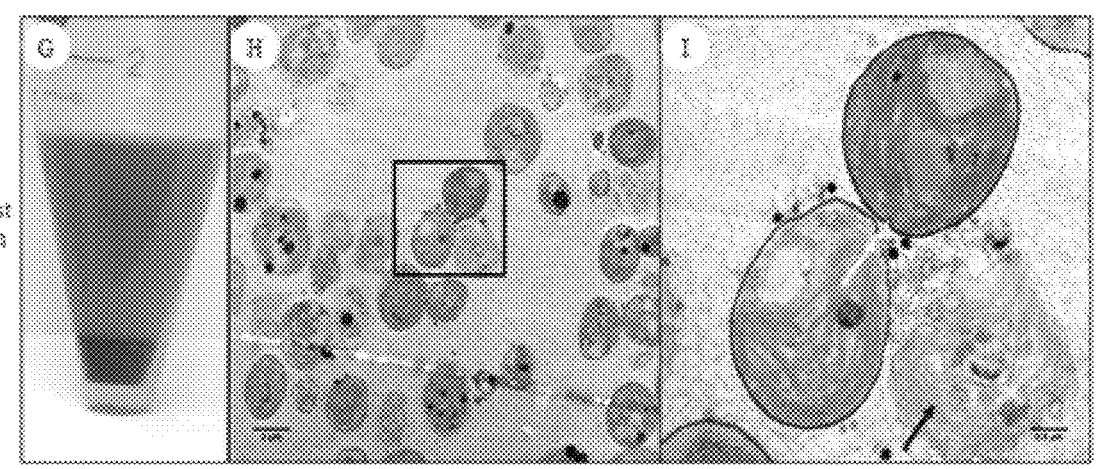

To investigate the infection at high algal density, algal suspensions were exposed to PBCV-1 at m.o.i. of 0.01 and samples were collected before infection, 43 hour post infection and 54 hour post infection for TEM observation. Successful cell infection and disruption were observed macroscopically and microscopically (FIG. 3). Before infection, *Chlorella* cells were intact and able to form pellets after centrifugation, leaving a clear and uncolored supernatant (FIG. 3A). As the number of lysed cells increased, the supernatant was colored by the released intracellular components (FIG. 3D) and when most of the cells were lysed the supernatant became turbid and colored (FIG. 3G).

We further investigated the effects of viral infection on *Chlorella* cell ultrastructure using TEM. Healthy *Chlorella* cells with integrated nucleus and undamaged cell walls were observed before the addition of virus (FIG. 3B,C). We started to see infected *Chlorella* cells 43 hours after the initial addition of PBCV-1 virus (FIG. 3E). The majority of *Chlorella* cells were still intact during this stage, but disorganized nucleus as well as virus capsids could be easily discovered in some cells (FIG. 3F). Empty (indicated by white arrow) and assembled (indicated by black arrow) virus capsids in hexagonal shape with a diameter of approximately 100 nm were identified in FIG. 3F, which were consistent with reported characteristics of PBCV-1 (Meints, Lee et al. 1986).

Normally, cell wall lysis and release of virus particles would occur after all viral capsids were assembled (Meints, Lee et al. 1986, Van Etten and Dunigan 2012). In the sample collected 54 hours post infection, most *Chlorella* cells were lysed and free viral particles were drifting in the solution. See FIGS. 2H and 2I. An empty virus capsid (white arrow in FIG. 3I) was found outside a segment of degraded algal cell wall with the contained viral DNA injected. The viral origin enzyme within the virus capsid was responsible for the digesting of algal cell wall (Meints, Lee et al. 1984), which indicated that algal virus was able to degrade algal cell walls and thus benefit lipid extraction.

Figure 7:
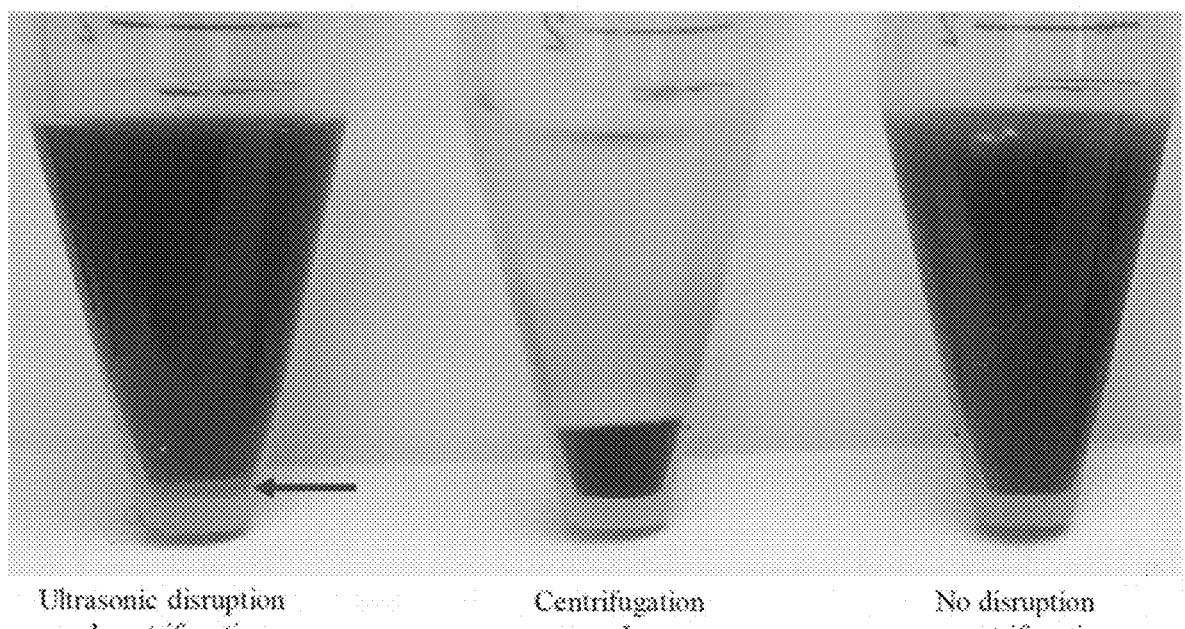
FIG. 7 shows the release of intracellular materials after sonication treatment. The white pellet (indicated by the arrow) in the left vial indicated that intracellular materials were mostly released after sonication as the undisrupted pellet showed (green) color (middle vial).

We also observed a lysed algal cell (FIG. 3I black arrow) next to the empty capsid, the intracellular components were clustered together while cell wall was hardly recognized. When zoomed out we found this was not a single case as a majority of the lysed cells still grouped intracellular components together with cell debris albeit the cell wall was highly deteriorated. See FIG. 3H. This could also be validated by the centrifugation result of the algal suspension. According to FIG. 3G, the light (green) color in the supernatant and the dark (green) color in the algae pellet indicated that only part of the chlorophyll was released into the aqueous environment while most of the chlorophyll stayed with the cell debris. A complete release of chlorophyll induced by ultrasonication would show dark green color in the supernatant and white color in the pellet (FIG. 7). Based on the above discussion, viral infection showed the ability to degrade cell wall and disrupt algal cell. Furthermore, intracellular materials such as lipids and chlorophyll tend to stay with lysed cells instead of releasing into the aqueous environment after viral disruption.

b. Infection Dynamics for Various Multiplicities

Viral infection works in a similar way to an autocatalysis reaction, so several cycles of replication are necessary to accumulate a sufficient amount of virus to infect all algal cells. It is obvious that increasing MOI can reduce the cycles of replication required in the disruption process, and thus reduce the processing time. However, increasing the MOI would add cost to the preparation of virus that is used for initial inoculation.

In order to balance the cost and processing time, the characteristics of viral life cycle such as replication time and virus burst size should be considered. For example, fast viral replication and large burst size can reduce the time used for virus accumulation. However, these characteristics are affected by inoculation conditions such as MOI and growth stage of host cells. Increasing MOI would cause the decreasing of burst size, while the growth stage of host cells would affect the speed of replication (Van Etten, Burbank et al. 1983). Normally, PBCV-1 can finish one replication in 6-8 hours and has a burst size of several hundred PFU (Van Etten and Dunigan 2012), but these characteristics are subject to change during the disruption process due to the increasing concentration of virus and high concentration of algae. Therefore, the infection behaviors with the proposed algal biomass content were investigated under various MOI.

The concentrated algal suspensions were exposed to PBCV-1 loadings from $1.66\pm0.04\times10^1$ PFU/mL to $1.66\pm0.04\times10^7$ PFU/mL. As illustrated in FIG. 4, the concentration of live algal cell in the control sample (with no virus addition) remained stable throughout the experiment, while complete disruption (no live cell) was achieved in all viral infected samples. Viral disruption could be triggered regardless of MOI but the disruption time was observed to be inversely proportional to the applied MOI. Under the infection conditions applied in this study, the time used for complete disruption ranged from 105 hours with highest MOI ($1.46\times 10^{-2}$) to 142 hours with lowest m.o.i. ($1.46\times 10^{-8}$). The increase of MOI by 6 orders of magnitude only saved 26% time used on disruption, which indicated low MOI might be a good choice for viral disruption. In real application of viral disruption, the virus rich lysate after disruption could be recycled and fed back to disruption tank, which can reduce the disruption time and save cost on virus preparation.

3. Viral Disruption for Lipid Extraction.

Based on the above discussion, although most of the oil is trapped in lysed cells after cell disruption, the highly deteriorated cell wall may no longer be a tough barrier for lipid extraction. To further evaluate the potential of using viral infection as a cell disruption method for lipid extraction from algal biomass, the mechanical strength and solvent permeability of algal cells after viral disruption were investigated.

a. Effect of Viral Disruption on Cell's Mechanical Strength

Figure 8:
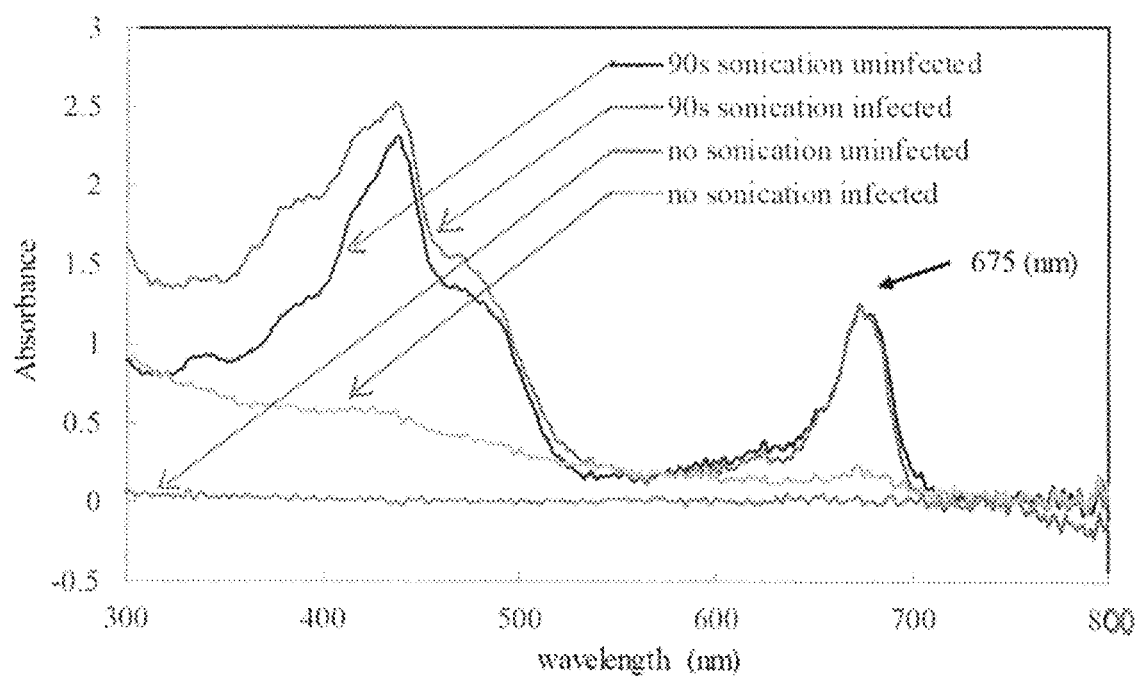
FIG. 8 is a graph showing the absorbance spectrum of supernatant after different treatments. The peak at 675 nm was used to quantify chlorophyll released from algal cells.

Since algal cells with reduced mechanical strength are more vulnerable to mechanical power, less energy is required for mechanical treatments to break cell walls and release intracellular lipids. The reduction in energy demand is beneficial to the overall economics of the lipid extraction process. In this study, sonication was employed to evaluate the effect of viral disruption on mechanical strength of algal cells. Sonication is able to break algal cells and cause the release of intracellular materials that tend to stay in the supernatant rather than precipitate in the pellet after centrifugation (illustrated in FIG. 7). In addition, the release of intracellular materials has been used to evaluate the level of cell breakage for *C. reinhardtii* (Gerde, Montalbo-Lomboy et al. 2012). Therefore, the amount of released intracellular materials was used as a means to quantify the mechanical strength of algal cells under various levels of sonication. The characteristic peak of released intracellular materials was located at 675 nm (the absorbance spectrum is presented in FIG. 8). Untreated and virus disrupted samples were subject to 420 and 150 seconds of ultrasonic treatments, respectively, until the absorbance measurements of supernatants were stabilized. The average of the last three absorbance measurements were used as the maximum absorbance when all intracellular materials were released. The efficiency of cell breakage at each sonication energy level was then calculated by dividing the absorbance reading by the maximum absorbance.

Figure 5:
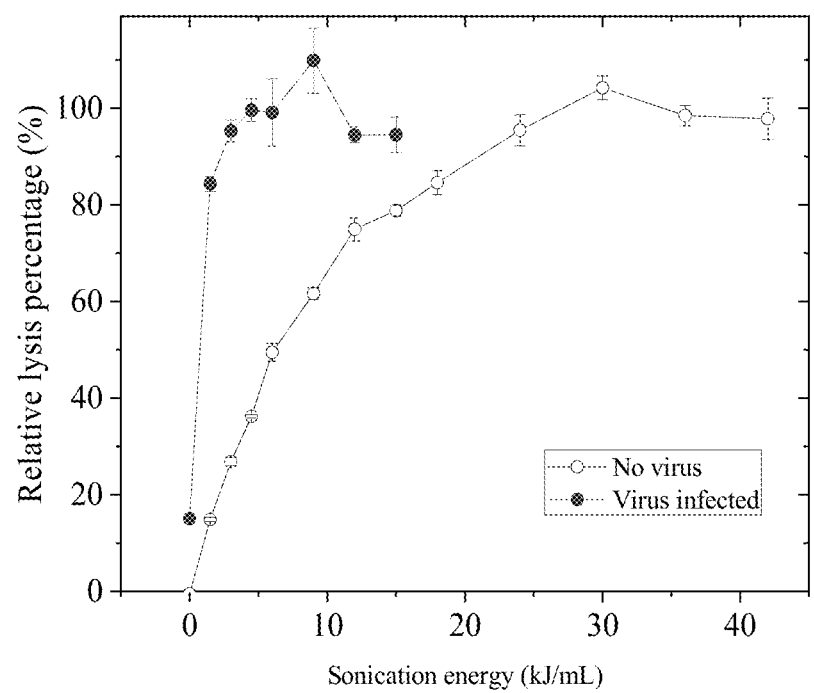
FIG. 5 is a graph showing viral treated and untreated efficiencies of intracellular material release at various ultrasonication time. Error bars represent the standard deviation of the mean.

The efficiency of cell breakage was plotted with sonication energy for untreated and virus disrupted samples (FIG. 5). For both untreated and virus disrupted samples, the efficiency of cell breakage surged at low energy levels, then the increase of efficiency slowed down as sonication energy increased, and finally the increase ceased when all cells were disrupted. Although the cell breakage patterns of untreated and virus disrupted samples were similar, the virus disrupted cells showed great reduction on their mechanical strength. To achieve 80% of cell breakage, the sonication energy for virus disrupted samples was 1.5 kJ/mL, which was 8.3% of the sonication energy 18 kJ/mL required for untreated samples. As for a complete cell breakage, the necessary sonication energy for virus disrupted samples was 4.5 kJ/mL, which was 15% of the 30 kJ/mL energy needed for untreated samples. According to these results, sonication appeared to be more efficient to release intracellular materials in virus disrupted suspensions, especially at low energy levels. As observed in FIGS. 3H and 2I, the virus disrupted algal cells were highly deteriorated and the crumbled cell wall could barely hold the intracellular materials in the cell envelope. Therefore, instead of consuming additional energy to break rigid cell wall, the intracellular materials in virus disrupted cells just need to be agitated out of the damaged cell envelope by sonication. Both the ultrastructure of virus disrupted cells as well as the results from sonication test indicated that viral disruption could significantly reduce the mechanical strength of algae cells.

b. Lipid Extraction with Organic Solvent

Figure 6:
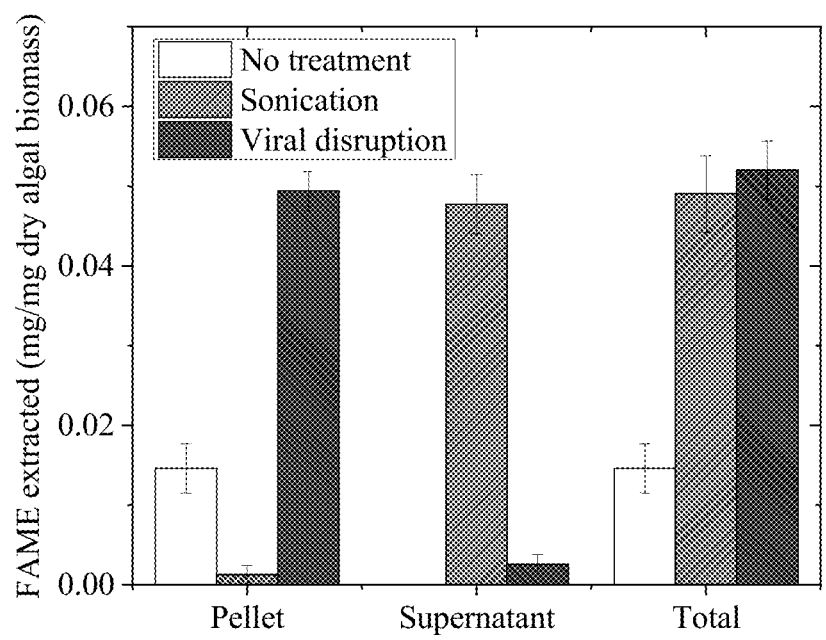
FIG. 6 is a graph depicting FAMEs yield in pellet, supernatant and total with various disruption methods. Error bars represent the standard deviation of the mean.

Lipids extraction via organic solvents was used to evaluate the performance of viral disruption, while no disruption and ultrasonic disruption were applied as the reference to the lower and upper limits of the performance. Lipids from the biomass pellet and the supernatant were analyzed separately to provide information about the distribution of lipids when different disruption methods were applied. As described previously, only detected FAMEs contents were used to calculate lipid yield. The highest lipid yields, $5.2\pm0.2$% wt/wt and $4.9\pm0.4$% wt/wt, were obtained by using both the viral disruption method and the ultrasonic disruption method (FIG. 6) as there was no statistically significant difference between the lipid yields from these two methods. However, the lipid yield with no treatment was $1.5\pm0.3$% wt/wt, which was only about 30% of the lipid yield when disruption methods were applied. The low lipid yield from undisrupted algal cells by applying direct solvent extraction was due to the surface charges of healthy algal cells, which kept them within water phase and prevented sufficient contact with the solvent (Kim, Yoo et al. 2013). On the contrary, algal cells subjected to ultrasonic disruption were ruptured into small pieces of cell debris, which eliminated the barrier between intracellular materials and organic solvent. Similarly, the virus disrupted cells that lost their surface charges and cell integrity could no longer impede the contact between intracellular lipids and solvent.

Viral disruption has demonstrated the ability to perform comparable cell disruption as sonication, however, lipids tend to be held within lysed cells after viral disruption rather than dispersed into the solution after ultrasonic disruption. According to the results reported in (FIG. 6). 100% and 95% of the lipids extracted with no disruption and viral disruption were from the biomass pellet, while over 97% of the lipid yield with ultrasonic disruption came from supernatant. In samples with no disruption, lipids were enveloped in intact cells thus they would undoubtedly precipitate to the bottom with the biomass. The ultrasonic process is capable of breaking cells into small pieces that are unable to be precipitated by centrifugation, and the cell debris can trap released intracellular materials such as lipids (Wang and Wang 2011, Gerde, Montalbo-Lomboy et al. 2012), which explained the high lipid content observed in the supernatant of ultrasonic disrupted samples. For virus disrupted samples, the distribution of lipid showed similar trend to undisrupted samples. Although the virus disrupted cell walls were highly damaged, lipids tended to stay in lysed cells rather than be released into the solution, which was consistent with the analysis with TEM as described before.

c. Effect of Viral Disruption on Composition of Fatty Acids

The viral infection process can reprogram the metabolic pathway of the host algae, which may affect the composition of extracted lipids. For example, it has been reported that a marine algal virus EhV is able to reprogram the metabolic pathway of their host *E. huxleyi* to synthesize more triglycerides (TAGs) after viral infection (Rosenwasser, Mausz et al. 2014, Malitsky, Ziv et al. 2016). Furthermore, algal viruses themselves are a possible source of lipids. PBCV-1 has been reported to contain a lipid membrane and another virus EhV that can infect *E. huxleyi* was reported to possess high content of TAGs (Van Etten and Dunigan 2012, Malitsky, Ziv et al. 2016).

TABLE 1

Fatty acids composition of extracted lipids with different disruption treatments

| | FAME yield ($10^{-3}$ mg FAME/mg dry biomass) | | |
|---|---|---|---|
| Fatty acids | No Treatment | Sonication | Viral disruption |
| C 15:0 | 1.21 ± 0.086 | 2.71 ± 0.023 | 2.77 ± 0.067 |
| C 16:0 | 2.33 ± 0.649 | 9.24 ± 1.359 | 9.27 ± 0.458 |
| C 16:1 | 4.11 ± 0.057 | 11.33 ± 0.317 | 11.98 ± 0.380 |
| C 17:0 | 1.80 ± 0.658 | 5.99 ± 0.647 | 7.65 ± 1.207 |
| C 17:1 | 1.30 ± 0.011 | 4.17 ± 0.099 | 4.72 ± 0.359 |
| C 18:2 | 1.30 ± 0.685 | 4.97 ± 1.014 | 4.79 ± 0.202 |
| C 18:3 | 2.58 ± 0.946 | 10.64 ± 0.976 | 10.84 ± 0.596 |

The FAMEs contents obtained from different disruption methods were analyzed statistically and viral disruption did not show significant influence on lipid contents. The FAMEs profiles for each disruption method and the detailed values are listed in Table 1.

The total yields obtained from both the supernatant and the pellet for each type of FAME were used to generate the FAMEs profile. The statistical analysis for each fatty acid was summarized in Table 2. According to the results, the yields of all types of fatty acids without disruption were much lower than the yields with disruption, which could be attributed to the low extraction efficiency caused by the intact cell wall. On the other hand, similar fatty acids profiles were obtained from both ultrasonic and viral disruption methods, which indicated that viral disruption was able to perform the disruption as efficiently as ultrasonic disruption without affecting the quality of extracted lipids. However, it is worth noting that the yields of fatty acids C 16:0, C 17:0, and C 17:1 obtained with viral disruption were higher than those obtained with ultrasonic disruption at an almost significant level.

The p-values obtained from an ANOVA test for these three fatty acids were 0.085, 0.062, and 0.104, respectively, which were close to the significance level of 0.05, showing that viral infection may have the ability to affect the quality of lipids in a way that is favorable to biofuel production.

TABLE 2

Statistical analysis results of ANOVA analysis of individual fatty acids

| | p-value of ANOVA tests | | |
|---|---|---|---|
| Fatty acids | No treatment and sonication | No treatment and viral disruption | Sonication and viral disruption |
| C 15:0 | 0.002 | 0.002 | 0.217 |
| C 16:0 | <0.001 | <0.001 | 0.085 |
| C 16:1 | 0.001 | <0.001 | 0.973 |
| C 17:0 | <0.001 | <0.001 | 0.062 |
| C 17:1 | 0.001 | 0.002 | 0.104 |
| C 18:2 | 0.005 | <0.001 | 0.773 |
| C 18:3 | <0.001 | <0.001 | 0.778 |

Nonetheless, the relatively low lipid yield with ultrasonic treatment may be due to the sonication induced lipid oxidation (Gerde, Montalbo-Lomboy et al. 2012). Therefore, the lipid content was not affected by viral disruption in this study, however, more in-depth investigations should be conducted in the future to explore the impact of virus on the lipid metabolic pathway of host algae.

4. Economical Aspects In addition to the comparable disruption performance, using viral lysis to disrupt wet algal biomass for lipid extraction has shown significant economic potential over other existing disruption methods reported in literature. The infection and lysis processes of algal biomass can be operated under normal temperature and pressure in wet biomass. The isolated virus massively proliferates in a short time to meet the demand of treatment. Part of the virus rich lysate after disruption can be recycled and fed to fresh wet biomass to save the time and cost in virus preparation. Therefore, viral disruption does not require the extensive energy and chemical input applied in physical and chemical disruption methods. Additionally, algal viruses can be acquired and maintained with minimal costs as compared to the high costs of enzymes that are available for cell wall degradation. Consequently, the moderate operation conditions and low cost of reagents have made viral disruption a competitive choice in large scale lipid extraction systems.

Those skilled in the art will recognize that numerous modifications can be made to the specific implementations described above. The implementations should not be limited to the particular limitations described. Other implementations may be possible.

The invention claimed is:

1. A method of extracting lipids from a wet microalgal biomass comprising algal cells, comprising:

inoculating the wet microalgal biomass with a matched algal virus, the matched algal virus being characterized in that the algal virus infects the algal cells and replication of the algal virus ruptures the algal cells of the microalgal biomass;

incubating the matched algal virus with the wet microalgal biomass to initiate virus infection of the algal cells and replication of the algal virus;

continuing to incubate the matched algal virus with the wet microalgal biomass until the virus replication has disrupted at least 90% of the algal cells within the wet microalgal biomass; and collecting crude lipids released from the disrupted algal cells.

2. The method of claim 1 in which said inoculating comprises adding the matched algal virus to the wet microalgal biomass at a virus-to-algae ratio of at least $1.46 \times 10^{-8}$.

3. The method of claim 2 in which said inoculating comprises adding the matched algal virus to the wet microalgal biomass at a virus-to-algae ratio of $1.46 \times 10^{-8}$ to $1.46 \times 10^{-2}$.

4. The method of claim 3 and which includes continuing to incubate the matched algal virus with the wet microalgal biomass until at least 99% of the algal cells have been disrupted.

5. The method of claim 4 in which said continuing to incubate is performed under conditions and for a time effective to disrupt at least 99.99% of the algal cells.

6. The method of claim 5 in which the wet microalgal biomass comprises at least 99% by weight water.

7. The method of claim 1 in which said collecting comprises solvent extracting the crude lipids.

8. The method of claim 1 and which, following the continuing step and preceding the collecting step, includes using centrifugation to separate the wet microalgal biomass into a solid phase and a liquid supernatant.

9. The method of claim 8 in which said collecting comprises solvent extracting the crude lipids from the supernatant.

10. The method of claim 9 in which said solvent extracting uses chloroform as the solvent.

11. The method of claim 10, and further including transesterification of the obtained crude lipids to the form of acid methyl esters (FAMEs).

12. A method of extracting lipids from a wet microalgal biomass comprising algal cells, comprising:
    inoculating the wet microalgal biomass with a matched algal virus, the matched algal virus being characterized in that the algal virus infects the algal cells and replication of the algal virus ruptures the algal cells of the microalgal biomass, the inoculating being at a virus-to-algae ratio of at least $1.46 \times 10^{-8}$, the wet microalgal biomass comprising at least 99% water;
    incubating the matched algal virus with the wet microalgal biomass to initiate virus infection of the algal cells and replication of the algal virus;
    continuing to incubate the matched virus with the wet microalgal biomass until the virus replication has disrupted at least 99% of the algal cells within the wet microalgal biomass; and
    solvent extracting crude lipids released from the disrupted algal cells.

13. The method of claim 12 in which, following the continuing step and preceding the solvent extracting step, includes using centrifugation to form a solid phase and a liquid supernatant, said solvent extracting being performed on the supernatant.

14. The method of claim 13 in which said solvent extracting uses chloroform as the solvent.

15. The method of claim 14, and further including transesterification the obtained crude lipids to the form of acid methyl esters (FAMEs).

16. The method of claim 4 which includes continuing to incubate the matched algal virus with the wet microalgal biomass under conditions to disrupt at least 99% of the algal cells within two weeks.

17. The method of claim 4 which includes continuing to incubate the matched algal cells under conditions to disrupt at least 99% of the algal cells within two hours.

18. The method of claim 1 and which, following the continuing step and preceding the collecting step, includes lysing the disrupted wet microalgal biomass.

19. The method of claim 12 and which, following the continuing step and preceding the collecting step, includes lysing the disrupted wet microalgal biomass.

20. The method of claim 19 which includes continuing to incubate the matched algal cells under conditions to disrupt at least 99% of the algal cells within two hours.

\* \* \* \* \*